United States Patent [19]
Rouanet et al.

[11] Patent Number: 5,864,923
[45] Date of Patent: Feb. 2, 1999

[54] METHOD OF FORMING PARTICLES USING A SUPERCRITICAL FLUID

[75] Inventors: Stephane Fabrice Rouanet, Hyde Park; William Edward McGovern, Duxbury, both of Mass.; Wanqing Cao, Alameda, Calif.; John M. Moses, Dedham; Angel L. Carrillo, Wellesley, both of Mass.; Irving M. Klotz, Evanston, Ill.

[73] Assignees: CF Technologies, Inc., Hyde Park; The Gillette Company, Boston, both of Mass.

[21] Appl. No.: 920,287

[22] Filed: Aug. 26, 1997

Related U.S. Application Data

[63] Continuation of Ser. No. 333,289, Nov. 2, 1994, abandoned, which is a continuation-in-part of Ser. No. 149,190, Nov. 8, 1993, abandoned.

[51] Int. Cl.⁶ .............................. B01D 9/00; B01D 17/00; C07C 7/10
[52] U.S. Cl. ......................... 23/295 R; 23/300; 424/65; 585/833
[58] Field of Search ........................ 423/495, 480, 423/659; 424/65, 67, 68, 69; 23/295 R, 300; 585/833

[56] References Cited

U.S. PATENT DOCUMENTS

| | | | |
|---|---|---|---|
| 2,249,767 | 7/1941 | Kistler | 252/373 |
| 3,879,569 | 4/1975 | Vitzthum et al. | 426/427 |
| 3,941,719 | 3/1976 | Yoldas | 252/463 |
| 3,944,658 | 3/1976 | Yoldas | 423/626 |
| 4,018,887 | 4/1977 | Danneman et al. | 424/47 |
| 4,148,812 | 4/1979 | Rubino et al. | 424/66 |
| 4,430,155 | 2/1984 | Kozischek et al. | 159/4 |
| 4,610,863 | 9/1986 | Tewari et al. | |
| 4,619,908 | 10/1986 | Cheng et al. | 502/214 |
| 4,622,310 | 11/1986 | Iacobucci | 502/208 |

(List continued on next page.)

FOREIGN PATENT DOCUMENTS

| | | |
|---|---|---|
| 0149816 | 7/1985 | European Pat. Off. . |
| 0171722 | 2/1986 | European Pat. Off. . |
| 0186149 | 7/1986 | European Pat. Off. . |
| O322687 A3 | 7/1989 | European Pat. Off. . |
| 880261 | 10/1961 | United Kingdom . |
| WO 90/03782 | 4/1990 | WIPO . |
| WO 95/01221 | 1/1995 | WIPO . |

OTHER PUBLICATIONS

C.J. Chang et al, "Solvent Expansion and Solute Solubility Predictions in Gas-Expanded Liquids", AIChE Journal, vol. 36, No. 6, Jun. 1990, pp. 939–942.

C.J. Chang et al, "Precipitation of Microsize Organic Particles from Supercritical Fluids", AIChE Journal, vol. 35, No. 11, Nov., 1989, pp. 1876–1882.

K.A. Larson et al, "Evaluation of Supercritical Fluid Extraction in the Pharmaceutical Industry", Biotechnology Progress, vol. 2, No. 2, Jun., 1986, pp. 73–82.

(List continued on next page.)

*Primary Examiner*—Gary P. Straub
*Attorney, Agent, or Firm*—Wolf, Greenfield & Sacks, P.C.

[57] ABSTRACT

A method for providing aerogels, and aerogels produced according to the method, is described. As one aspect, antiperspirant compounds that are in aerogel form, and antiperspirant and deodorant compositions including such salts, are described. The method involves contacting a solution containing material to be processed with a species selected to precipitate the material and selected so as to be miscible with the solvent system of the solution. After the material is precipitated, the material may be washed with the precipitating species until it is substantially free of solvent system. Then, the precipitating species containing the material precipitate is taken above its critical point, and the supercritical fluid is exhausted above its critical temperature. Alternately, a separate isolating species is introduced to displace the precipitating species, or the precipitating species/solvent system mixture. The isolating species then is taken above its critical point, and exhausted above its critical temperature. The invention provides for batch or continuous processes.

18 Claims, 5 Drawing Sheets

U.S. PATENT DOCUMENTS

| | | | |
|---|---|---|---|
| 4,667,417 | 5/1987 | Graser et al. | 34/9 |
| 4,695,451 | 9/1987 | Straw et al. | 34/9 |
| 4,717,708 | 1/1988 | Cheng et al. | 502/233 |
| 4,748,220 | 5/1988 | Hartmann et al. | 526/89 |
| 4,845,056 | 7/1989 | Yamanis | 507/12 |
| 4,944,837 | 7/1990 | Nishikawa et al. | 156/646 |
| 4,954,334 | 9/1990 | Pugh et al. | 424/68 |
| 4,961,913 | 10/1990 | Sullivan | 423/351 |
| 4,987,243 | 1/1991 | Kawam et al. | 556/27 |
| 4,997,804 | 3/1991 | Pekala | 502/418 |
| 5,011,819 | 4/1991 | Leibovitz | 505/1 |
| 5,028,363 | 7/1991 | Nishio et al. | 264/28 |
| 5,043,280 | 8/1991 | Fischer et al. | 435/235.1 |
| 5,045,289 | 9/1991 | Fernando et al. | 423/21.1 |
| 5,066,684 | 11/1991 | LeMay | 521/64 |
| 5,116,883 | 5/1992 | LeMay | 521/178 |
| 5,156,833 | 10/1992 | Osugi et al. | 424/46 |
| 5,158,986 | 10/1992 | Cha et al. | 521/82 |
| 5,232,689 | 8/1993 | Katsoulis | 424/66 |
| 5,238,671 | 8/1993 | Watson et al. | 423/397 |
| 5,360,478 | 11/1994 | Krukowis et al. | 117/68 |
| 5,389,263 | 2/1995 | Gallagher et al. | 210/729 |
| 5,391,364 | 2/1995 | Cogliati | 423/335 |
| 5,395,805 | 3/1995 | Droege et al. | 501/72 |

OTHER PUBLICATIONS

T.W. Randolph et al., "Sub–Micrometer–Sized Biodegradable Particles of Poly(L–Lactic Acid) via the Gas Antisolvent Spray Precipitation Process", Biotech Prog, vol. 9, 1993, pp. 429–435.

J.W. Tom et al., "Particle Formation With Supercritical Fluids—A Review", J. Aerosol Sci., vol. 22, 1991, pp. 555–584.

J.M. Moses et al., "Development and processing of aerogels in a windowed autoclave", Journal of Non–Crystalline Solids, vol. 145, 1992, pp. 41–43.

P.G. Debenedetti, "Supercritical Fluids as Particle Formation Media", Abstract of Meeting Presentation, Published Jul., 1993.

H.D. Gesser et al., "Aerogels and Related Porous Materials", Chemical Reviews, 1989, vol. 89, No. 4, pp. 765–788.

J.N. Armore et al., "Metallic Aerogels: A Novel Synthesis of Very Fine Copper Powder", Materials Letters, vol. 4, No. 8,9, Aug. 1986, pp. 373–376.

E.I. Ko, "Aerogels as catalysts and catalyst supports", Chemtech, Apr. 1993, pp. 31–36.

V.J. Krukonis et al., "Exploratory Development on a New Process to Produce Improved RDX Crystals; Supercritical Fluid Anit–Solvent Recrystallization" Ballistic Research Laboratory Contract Report BRL–CR–606, May 2, 1988.

PHASEX "Supercritical Fluids Assist in Particle Formation", (Apr. 1990) p. 19 *Chemical Engineering(International Edition)*, vol. 97, No. 4.

Gallagher et al., "Gas Antisolvent Recrystallization: New Process to Recrystallization Compounds Insoluble in Supercritical Fluids"—Supercritical Fluid Science and Technology, ACS Symposium Series 406, *American Chemical Society: Washington, DC,* (1989) pp. 334–354.

Debendetti et al. "Applicantion of Supercritical Fluids for the Production of Sustained Delivery Devices" (May 1, 1993) pp. 27–44, *Journal of Controlled Release* vol. 24.

Yeo et al., "Formation of Microparticulate Protein Powders Using a Supercritical Fluid Antisolvent" (Feb. 5, 1993) pp. 341–346, *Biotechnology and Bioengineering*, vol. 41, No. 3.

Liou et al., "Separation of Anthracene from Crude Anthracene Using Gas Antisolvent Recrystallization", (Aug., 1991) pp. 1277–1289, *Separation Science and Technology* vol. 27, No. 10.

Dixon et al., "Polymeric Materials Formed by Precipitation with a Compressed Fluid Antisolvent" (Jan. 1993) *AIChE Journal*, vol. 39, No. 1.

Rangarajan et al., "Production of Aerogels", (1991), pp. 1–6, *The Journal of Supercritical Fluids* vol. 4, No. 1.

Rouanet ["Supercritical Fluids Gas Anti–Solvent"—Literature review, abstracts, 8 pp].

METHOD OF FORMING PARTICLES USING A SUPERCRITICAL FLUID

REFERENCE TO RELATED APPLICATION

This application is a continuation of application Ser. No. 08/333,289, filed Nov. 2, 1994, now abandoned, which is a continuation-in-part of application Ser. No. 08/149,190, filed Nov. 8, 1993, now abandoned, incorporated herein by reference.

FIELD OF THE INVENTION

The present invention relates generally to methods of forming particles by precipitation using an isolating species which then is exhausted above its critical point, to aerogels formed by the methods, and to the use of such aerogels as, for example, antiperspirants.

BACKGROUND OF THE INVENTION

The term "supercritical fluid" defines a physical state of a particular species that exists above that particular species' critical point. The critical point of a species is that point on an equilibrium diagram at the intersection of the critical temperature and critical pressure of the species. The critical temperature of a species is defined by that temperature above which the species cannot exist as a liquid. The pressure that must be applied to cause condensation of the species at the critical temperature is the critical pressure, that is, the critical pressure is the vapor pressure of the species at its critical temperature. Thus, a supercritical fluid is defined as a phase existing above the critical temperature and above the critical pressure of a particular species.

Supercritical fluids exhibit unusual characteristics different from certain characteristics exhibited by liquids, solids, or vapors, and these unique characteristics have been exploited in a variety of methods for processing a variety of substances. For example, U.S. Pat. No. 5,028,363 describes an extraction process using supercritical carbon dioxide. Extraction is particularly aided by the use of supercritical fluids in that the solubility of certain substances in supercritical fluids can be highly sensitive to slight variations in temperature and pressure near the critical point. Often, a chemical reaction may be carried out in a supercritical carbon dioxide medium, followed by extraction to produce a product. U.S. Pat. No. 5,045,289 describes such a process, in which a rare earth-bearing compound is reacted to form a carbonate under supercritical conditions. U.S. Pat. No. 4,748,220 describes a free-radical polymerization reaction carried out in supercritical carbon dioxide, resulting in polymer powder.

Additionally, supercritical fluids find use in silica gel drying. According to a typical procedure a gel of an ethyl oxide of silicon is hydrolyzed in a liquid phase, then subjected to supercritical drying.

The processing of various articles in supercritical fluids has been described. For example, a method of forming a patterned resist film is described in U.S. Pat. No. 4,944,837. Microcellular foams have been processed using supercritical fluids, for example as described in U.S. Pat. Nos. 5,066,684; 5,116,883; and 5,158,986. Processing of foods using supercritical fluids is known, for example, the decaffination of coffee as described in U.S. Pat. No. 3,879,569.

Supercritical fluids have also found use in so-called "supercritical drying" of organometallics. In a typical supercritical drying procedure, residual solvent is removed from pores of particulate material to be collected, by washing the material with a liquefied gas to remove the residual solvent, and the liquefied gas then is exhausted above its critical temperature.

In many areas of materials processing a need exists for providing materials having a very high surface area, Very high surface area is important in many fields for rapid and efficient chemical reaction, absorption, delivery or analysis of various species, and the like. Additionally, a need exists for the processing of such materials in a way that results in a very fine powder that is easily flowable, and easily transferable from one container to another.

A common procedure for attaining relatively high-surface-area particulate material is spray drying. In a typical spray drying procedure, a material to be collected is dispersed within or dissolved in a solvent, and the solution or dispersion is sprayed as a very fine mist into a chamber within which the solvent is evaporated. The material then is collected. During the evaporation process, the material "collapses". That is, it rapidly agglomerates when the fine droplet within which it is carried evaporates. Thus, in spray drying techniques, the surface area of the material collected is generally not maximized. Additionally, spray drying requires large areas of workspace and solvent is not easily recoverable.

Particles produced by some of these methods have been referred to as aerogels.

Antiperspirant compositions are used to reduce perspiration. The compositions typically are applied to the skin in the form of an aerosol, solid stick, semi-solid stick, gel stick, cream, or roll-on. Antiperspirant compositions typically include a dermatologically acceptable anhydrous carrier and an amount of an antiperspirant compound that is effective to reduce perspiration. Common antiperspirant compounds include aluminum salts, zirconium salts, and aluminum-zirconium salts.

Two antiperspirant compounds commonly used in antiperspirant compositions are aluminum chlorohydrate and aluminum-zirconium tetrachlorohydrex Gly. These compounds typically are non-porous and have a surface area of between about 1 $m^2/g$ and 6 $m^2/g$, an average bulk density of between about 1.4 g/cc and 1.8 g/cc and an average particle size of between 1 micron and 80 microns.

SUMMARY OF THE INVENTION

The present invention provides a method of forming particles including, but not limited to, aerogels by contacting a solution of the material in a solvent system with a species within which the material is insoluble and that is inert with respect to the material to form a mixture precipitating the material, and isolating the material under supercritical conditions. The step of isolating the material may be carried out by maintaining the precipitating species above its critical point as a supercritical fluid, and exhausting the precipitating species above its critical temperature. If the precipitating species is provided as a gas or liquid, it is taken above its critical point to form a supercritical fluid and the exhausted above its critical temperature. The precipitating species can be maintained above its critical point be controlling the temperature and pressure to which it is subjected. If the precipitating species is a liquid or gas when it serves to precipitate the material, it can be taken above its critical point by subjecting it, generally in a pressure vessel, to a temperature higher than its critical temperature, and a pressure higher than its critical pressure.

The solution containing the material to be processed is defined by a solvent system selected to be miscible with the precipitating species, and selected to dissolve the material to be processed. The solution, formed by partially or fully dissolving the material to be processed in the solvent system, may be a homogeneous solution, or a solution containing a variety of dissolved materials. The solution is contacted by an amount of precipitating species sufficient to precipitate the material.

The precipitating species is selected to be miscible with the solvent system, and also is selected so as to precipitate the material to be processed. That is, the material to be processed is insoluble in the precipitating species. And, according to this embodiment, the material is insoluble in the precipitating species even if the precipitating species is taken above its critical point. Additionally, the precipitating species is selected to be inert with respect to the material. The precipitating species also is selected so as to have a critical temperature lower than the degradation temperature of the material processed.

Once precipitation has been achieved, the solvent system is displaced by the precipitating species to a predetermined extent consistent with acceptable levels of residual solvent in the product. The precipitating species then is taken above its critical point, and exhausted above its critical temperature.

According to another embodiment of the invention, an isolating step is carried out by displacing the precipitating species and the solvent system with an isolating species, taking the isolating species above its critical point, and exhausting the isolating species above its critical temperature. According to this embodiment, the precipitating species is not taken above its critical point. Therefore, the solubility of the material in the precipitating species at or near the critical point of the precipitating species is not important. The solvent system may be fully displaced by the precipitating species, and the precipitating species displaced by the isolating species, or the isolating species may displace a mixture of the solvent system and the precipitating species. According to the former method, the isolating species is selected to be miscible with the precipitating species. According to the latter method, the isolating species is selected to be miscible with the precipitating species and the solvent system.

No fluid phase/fluid phase interface should be allowed to form during contact of the solution containing the material with the precipitating species, nor during displacement by the isolating species.

Particles formed in the inventive methods are characterized by their large surface area, low bulk density, high porosity, and small particle size.

One aspect of the invention features material, for example antiperspirant compounds, having high surface area (generally greater than 10 m$^2$/g). Preferred material has a surface area of between 10 m$^2$/g and 1800 m$^2$/g. More preferred material has a surface area of between 50 m$^2$/g and 1200 m$^2$/g, and most preferred material has a surface area of between 100 m$^2$/g and 1000 m$^2$/g.

Another aspect of the invention features material, for example antiperspirant compounds, having low bulk density. Some preferred material has a bulk density less than 1.2 g/cc, more preferably between 0.01 g/cc and 0.75 g/cc, and most preferably between 0.1 g/cc and 0.5 g/cc. Other preferred material has a bulk density less than 1.0 g/cc, more preferably between 0.005 g/cc and 0.5 g/cc, and most preferably between 0.01 g/cc and 0.1 g/cc.

Another aspect of the invention features material, for example antiperspirant compounds, having high porosity.

High porosity, as used herein, means that the compound has one or more of the following attributes: a pore volume of at least 0.1 cc/g, preferably between 0.15 cc/g and 1.9 cc/g, more preferably between 0.3 cc/g and 1.7 cc/g; a pore size of above 1 nm, preferably between 2 nm and 350 nm, more preferably between 5 nm and 100 nm; and a percent pore of at least 10%, preferably between about 20% and about 90%.

Another aspect of the invention features material, for example antiperspirant compounds, in the form of submicron sized particles. Preferred particulate material has an average particle size of less than 0.5 micron. More preferred particulate material has an average particle size of less than 0.2 micron, and most preferred particulate material has an average particle size of between 0.005 micron and 0.07 micron.

The term "aerogel" as used herein, means a material that has two or more of the high surface area, low bulk density, high porosity, and small particle size features described above. For example, the aerogel can be material having a small particle size and one of high surface area, low bulk density, and high porosity. Preferred aerogel materials include three or more of these features. More preferred aerogel materials include all four of these features.

The surface area of the material may be measured in accordance with ASTM Designation D1993-91. The bulk density of the material may be measured in accordance with ASTM Designation C493-86 or, alternatively, by determining the mass to volume ratio of a dry sample of powder under ambient conditions. Thus, the material has a bulk density of, for example, less than 1.2 g/cc if the bulk density of the material measured in accordance with either or both methods is less than 1.2 g/cc. The absolute density may be measured in accordance with ASTM Designation D2638-91. The pore size of the material may be measured in accordance with ASTM Designation D4641-88. The pore volume may be determined from the adsorption isotherm obtained in accordance with ASTM Designation D-4222. The X axis of the isotherm is P/P$_o$, and the Y axis is nitrogen volume adsorbed. The maximum volume of nitrogen adsorbed at standard temperature and pressure (STP) is determined from the isotherm by finding the point on the isotherm at which P/P$_o$ is no longer changing appreciably, and obtaining the nitrogen volume adsorbed from the Y axis. This value then is multiplied by $$\frac{0.0012506 \text{ g/cc(density of N}_2 \text{ at } STP)}{0.812077 \text{ g/cc(density of N}_2 \text{ at liquid state)}}$$

to provide the pore volume. Percent pore is determined from the absolute density (AD) and the bulk density (BD) (percent pore=[1−(BD/AD)]×100). Finally, the average particle size of material is determined by examining a scanning electron micrograph having an appropriate magnification (typically between 5,000× and 50,000×) of the material and determining the average diameter of the individual particles.

According to one embodiment, the invention relates to antiperspirant compounds that are in aerogel form, to antiperspirant and deodorant compositions that include aerogel antiperspirant compounds suspended in a dermatologically acceptable carrier, and to methods of controlling perspiration or preventing malodor by applying aerogel antiperspirant compounds to the skin.

The aerogel antiperspirant compounds of the invention generally are self-suspending and have long settling times. As a result, typically there is no need to use a suspending agent when, for example, the salts are incorporated into aerosol, liquid, or semi-solid stick antiperspirant compositions. Antiperspirant compositions including the aerogel antiperspirant compounds generally can be formulated with fewer components (e.g., suspending agents), and as a result antiperspirant compositions including the compounds are easy to process. Moreover, the aerogel compounds tend not to clog the spraying mechanism commonly used to apply aerosol antiperspirant compositions.

The aerogel antiperspirant compounds also provide antiperspirant and deodorant compositions having excellent aesthetic properties. For example, compositions including the aerogel salts have a dry feel after application. In addition, such compositions have a smooth feel during application. Moreover, antiperspirant and deodorant compositions including the aerogel compounds typically leave little or no white residue after application. Finally, the aerogel compounds provide a clear composition when incorporated into some anhydrous carriers. The aerogel antiperspirant compounds may also retain fragrance for a substantial period of time after application to the skin.

The aerogel antiperspirant compounds generally have excellent antiperspirant efficacy.

Other features and advantages of the invention will be apparent from the description of the preferred embodiment thereof, and from the claims.

DETAILED DESCRIPTION OF THE INVENTION

Figure 1:
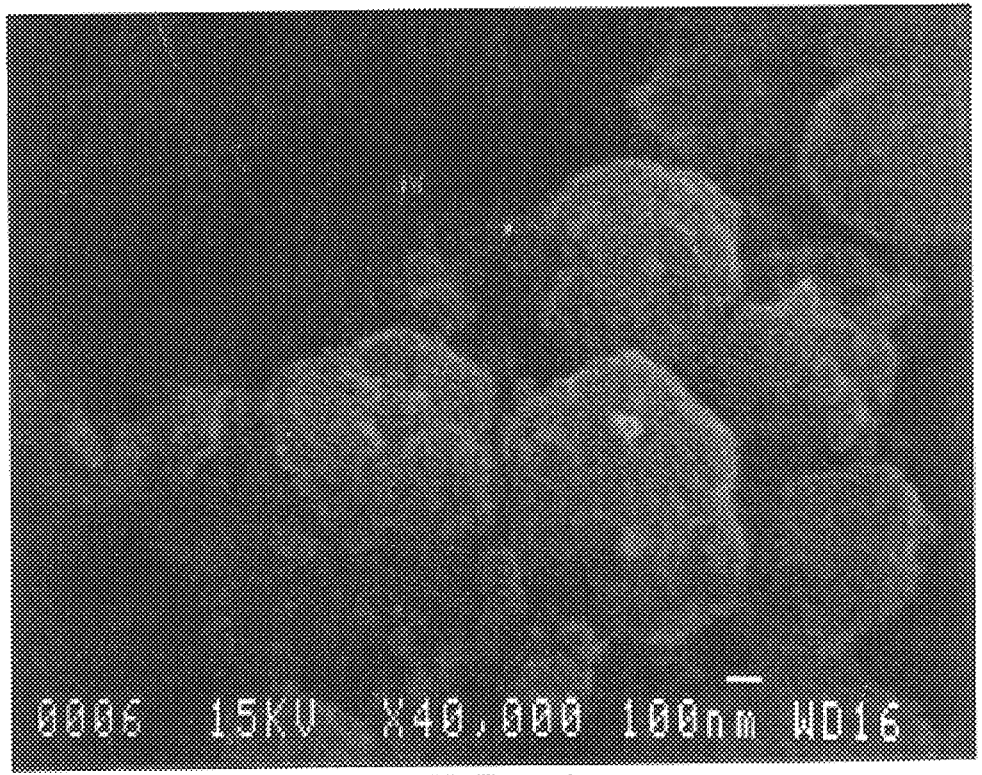
FIG. 1 is a photocopy of a scanning eletron micrograph of zinc acetate in aerogel form.
Figure 2:
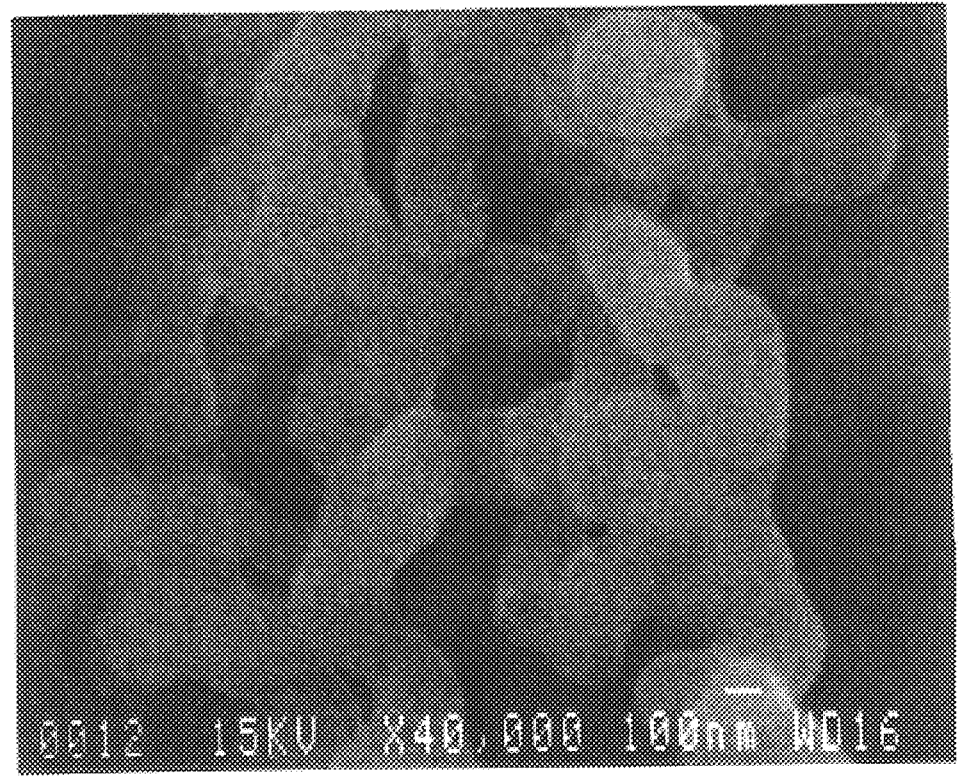
FIG. 2 is a photocopy of a scanning electron micrograph of eosin in aerogel form.
Figure 3:
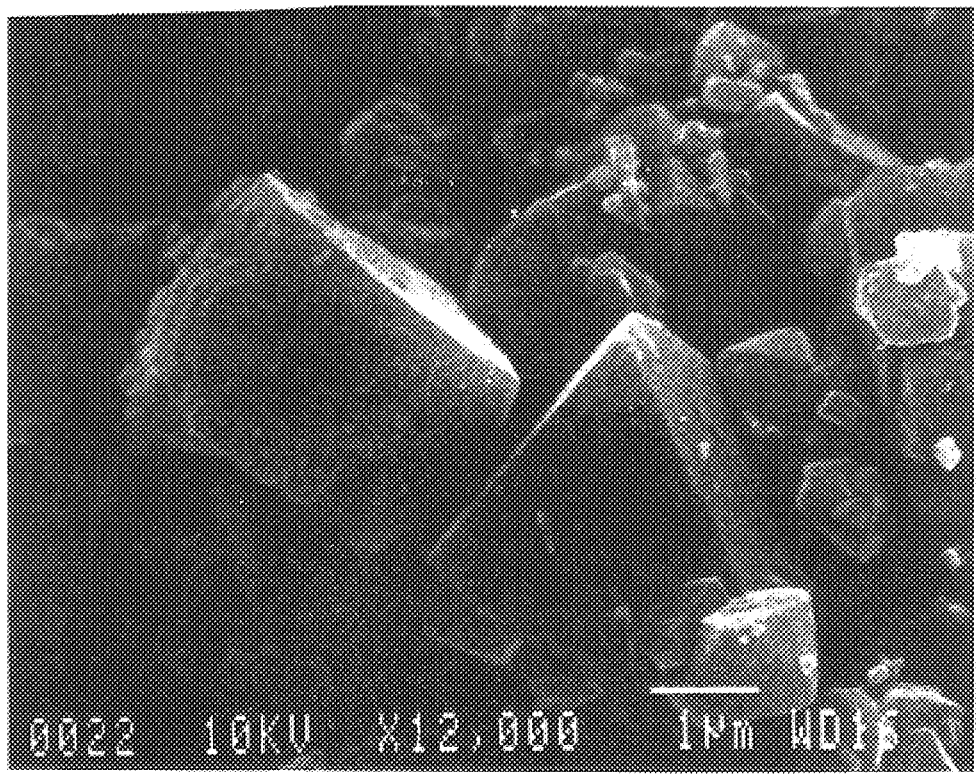
FIG. 3 is a photocopy of a scanning electron micrograph of fullerite in aerogel form.
Figure 4:
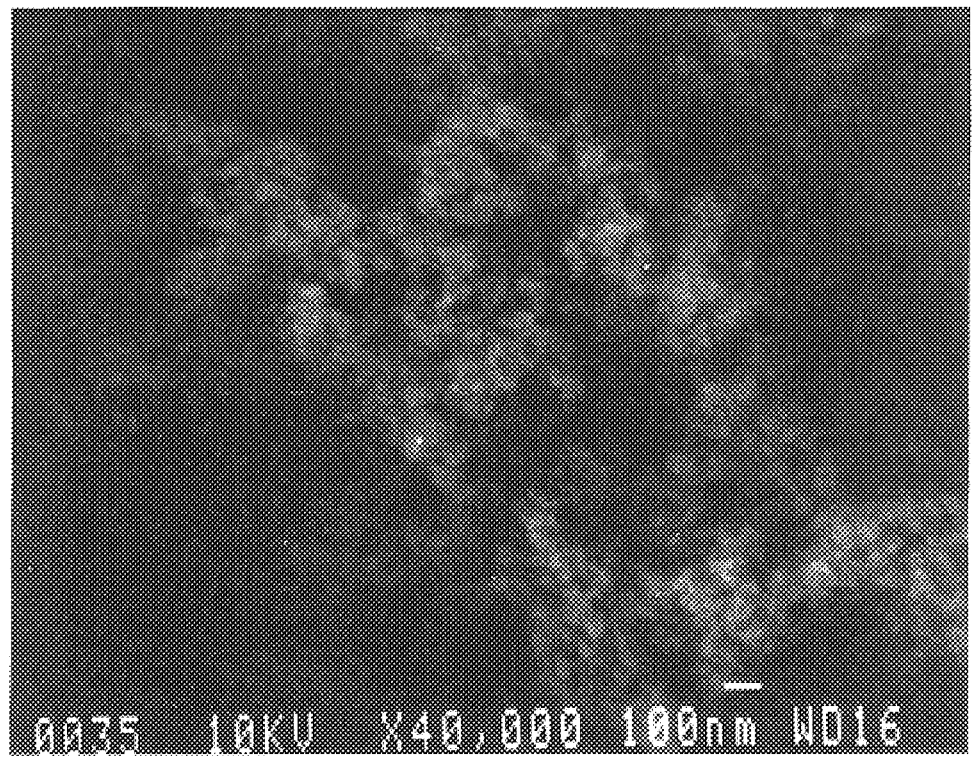
FIG. 4 is a photocopy of a scanning electron micrograph of aluminum/zirconium salt in aerogel form.
Figure 5:
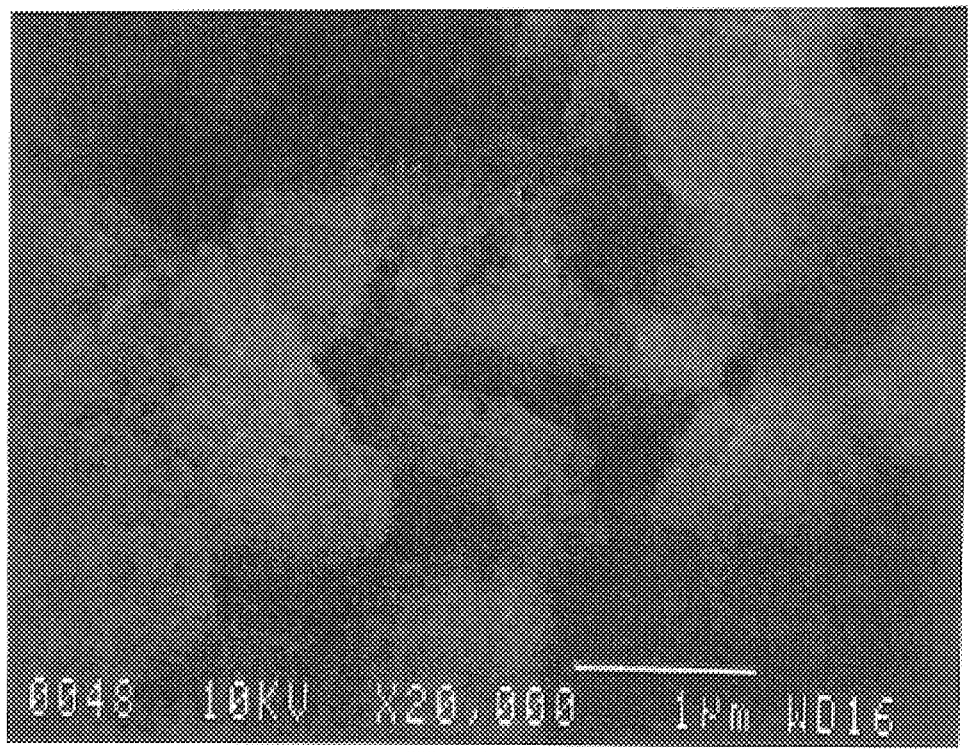
FIG. 5 is a photocopy of a scanning electron micrograph of copper chloride in aerogel form.
Figure 6:
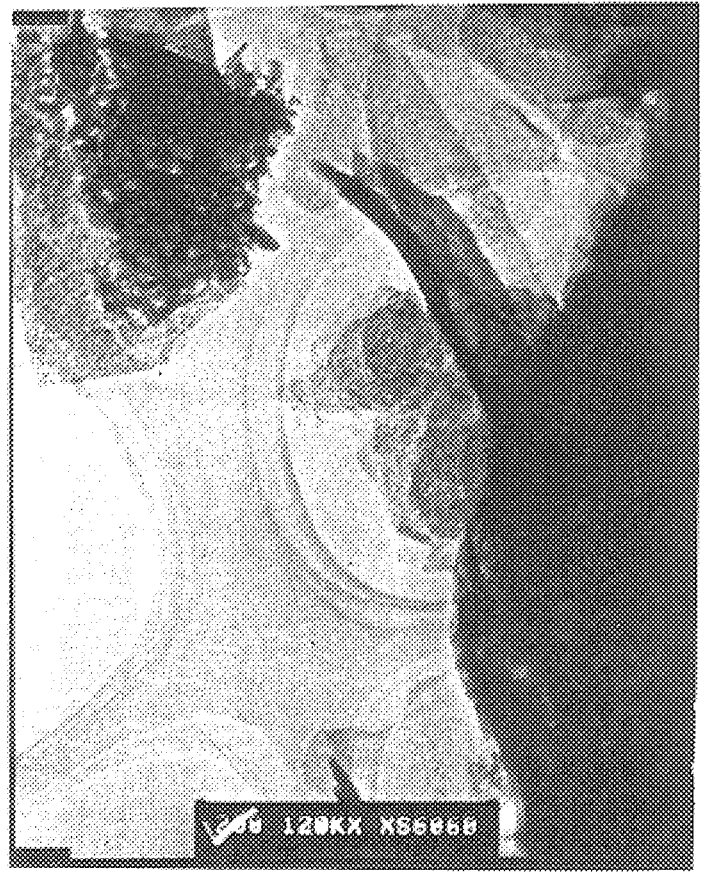
FIG. 6 is a photocopy of transmission electron micrograph of zinc oxide in aerogel form.

The present invention provides a method of obtaining high surface area particles, such as aerogels, in very pure form. The invention finds use in the processing of materials in a wide variety of fields, particularly in a variety of rapid reacting materials fields such as antiperspirants, pharmaceuticals, topicals, catalysis, assay support surfaces, preservation, coatings, thin films, electronics, superconductors, semiconductors, dielectrics, ceramics, dopants, membranes, and the like. In each of these fields, it is generally advantageous to provide an inert material having a very high surface area, for example so as to provide a support which may be derivatized for a further process, or to provide a reactive substance itself in high surface area form. For many applications, the support for the reactive material must be highly pure; the presence of residual solvent or other contaminants in the pores of such materials may be highly disadvantageous in certain circumstances.

According to one embodiment, the invention involves contacting a solution defined by a material to be processed in a solvent system with a precipitating species that is miscible with the solvent system defining the solution, and that precipitates at least one species from solution. The solvent system then is displaced by the precipitating species which then is taken above its critical point to form a supercritical fluid, and then is exhausted above its critical temperature. The solution may be a homogeneous solution or may be a solution containing a plurality of materials dissolved in a solvent system. When the solution contains a plurality of materials, it is desirable according to some embodiments that only one of the materials be precipitated when the solution is contacted with the precipitating species. Thus, the invention also provides for selective precipitation from a multi-species solution.

According to another embodiment, the precipitating species need not be taken above its critical point and exhausted, but another, isolating species may displace the precipitating species, the isolating species then being taken above its critical point and exhausted above its critical temperature. When such a second, isolating species is employed, the isolating species partially or fully displaces the precipitating species and, if the precipitating species has not already displaced the solvent system, the isolating species displaces the solvent system as well. Typically, the precipitating species forms a mixture with the solvent system and precipitates the material, and the mixture of the solvent system and precipitating species is displaced by the isolating species, then the isolating species is taken above its critical point and exhausted above its critical temperature.

To achieve the advantageous aerogels of the invention, the precipitating species must be miscible with the particular solvent system selected in the preparation of the solution. As used herein, the term "miscible" is meant to define a situation in which no fluid phase/fluid phase interface exists. Miscibility generally may be achieved even if the solvent system includes a component in a small amount, for example, less than 10 percent, that is completely immiscible with the precipitating species. Preferably, any component of the solvent system that is immiscible with the precipitating species is present in the solvent system in an amount less than 5 percent. Additionally, the isolating species, if it differs from the precipitating species, must be miscible with the precipitating species. If the precipitating species and solvent system exist as a mixture, that is, if the precipitating species does not fully displace the solvent system, the isolating species must be miscible with the solvent system/precipitating species mixture.

Additionally, to effect the precipitation step, the material to be processed and the precipitating species must be selected in conjunction with each other so that the material is insoluble in the precipitating species. As used herein, the term "insoluble" may be defined by the tolerable loss limit of the process. That is, if a particular process may be carried out economically even if 50 percent of the material to be processed is lost, and all other steps of the process exhibit nearly quantitative yields, the material may be soluble in the precipitating species to the extent that 50 percent of the material is dissolved by the precipitating species. Generally, however, the precipitating species is selected such that the material to be processed is insoluble therein at less than one wt %. When the precipitating species and material to be processed are selected so that the material is completely insoluble in the precipitating species, economy of the process is maximized as a maximum of material is collected. If the precipitating species is gas, virtually pure solvent system is recovered essentially quantitatively. This will become more apparent from the description below with reference to the figures.

Additionally, both the precipitating species and the isolating species, if they differ, are selected so as to be inert with respect to the material to be processed. The material to be processed should undergo no chemical reaction during any step of the inventive process. Thus, the inventive process can produce fine, high surface area powder from a solution, without chemical reaction.

If the precipitating species also serves as the isolating species, that is, if the precipitating species is taken above its critical point and exhausted above its critical temperature to isolate the material product, the precipitating species is added in an amount sufficient to displace the solvent system during or following precipitation, and according to a particularly preferred embodiment to completely remove any trace of solvent so as to produce product of the highest purity. This displacement may be achieved by effecting precipitation, and continuously introducing precipitating species into a vessel within which precipitation is effected while removing the resultant precipitating species/solvent system mixture through an outlet port blocked by a filter. Alternately, precipitating species may be continually introduced into a vessel while the precipitating species/solvent system is decanted, removed via a centrifugal separator, through a filter, or the like. According to one convenient method of decanting, the precipitating species is introduced into or near the bottom of a vessel while the precipitating species/solvent system mixture is removed from the top of the vessel, with a flow rate through the vessel low enough that precipitated product remains in the vessel.

According to an embodiment of the invention in which a precipitating species is employed, followed by employment of a different isolating species, the isolating species is added while the resultant isolating species/precipitating species or isolating species/precipitating species/solvent system mixture is decanted, removed via a centrifugal separator, removed through a filter, or the like. The isolating species is preferably added in an amount sufficient to completely remove any trace of solvent system and precipitating species, so as to produce product of the highest purity.

When different precipitating species and isolating species are used, a suspension of the material in the precipitating species can be concentrated to form a cake before the precipitating species is displaced by the isolating species. Economy in the process can be maximized in this manner, as the density of material introduced into an isolation vessel can be maximized. Optionally, the cake can be diluted with the precipitating species or another inert species that is miscible with the isolating species prior to isolation and supercritical exhausting. "Cake" is meant here to define a paste-like, highly concentrated mixture of the precipitate and the precipitating species (or other inert species).

In accordance with this procedure, a precipitating species should be selected that does not diminish advantageous morphological features of the precipitate when the suspension of the precipitate in the precipitating species is concentrated to form a cake. Generally, selection should be made such that the surface area of the precipitate is not reduced beyond acceptable levels during cake formation and subsequent optional dilution and supercritical isolation.

A relatively simple test to screen for a solvent system and precipitating species suitable for use in accordance with this embodiment is to dissolve material to be processed in a predetermined amount of a solvent system, add a predetermined amount of a precipitating species, observe the formation of precipitate, and observe the speed of sedimentation of the precipitate. Generally, a solvent system/ precipitating species mixture that results in formation of finely-divided precipitate that does not settle quickly will be suitable for concentration of the precipitate into a cake and subsequent supercritical isolation without loss of advantageous surface morphological features. According to this test, the precipitate should not settle appreciably within 30 seconds. Preferably, the precipitate should not settle within two minutes, more preferably not within 30 minutes, and most preferably the precipitate will not settle from the mixture appreciably after standing for 8 hours. A control may be carried out by adding precipitating species to solvent system that does not contain the material in solution and observing the characteristics of a beam of light passing through the mixture. If during this screening test it is difficult visually to determine whether a precipitate has formed (whether a suspension is present in the mixture), a relatively columnar beam of light (for example from a small flashlight) can be passed through the mixture. If the beam emerges as a column, then precipitation has not occurred or has occurred to a very slight extent. If the beam is diffracted and emerges diffusely, as a cone for example, then precipitation has occurred.

Another screening test is to concentrate a suspension of the material in the solvent system/precipitating species into a cake, and then re-suspend the precipitate in the same mixture. The material should be readily and rapidly re-suspended, and should not settle more quickly after re-suspension than in the mixture prior to concentration. Still another screening test is to extract solvent system/precipitating species from the cake and to determine whether the material has dissolved therein to an appreciable extent. No appreciable dissolving of the material is an indication of selection of suitable solvent system and precipitating species. Additionally, as a general rule, selection should be made such that the solvent system/precipitating species mixture is a relatively good anti-solvent to the material. Properties of the solvent system and precipitating species can be measured routinely, or determined with reference to common chemical supply catalogs, the Merck Index, the Handbook of Chemistry and Physics (C.R.C. Press), or the like.

Concentration of the suspension to form a cake is most easily effected by centrifugation, and should be carried out to form a cake that contains at least about 15 wt % of the precipitate, preferably at least about 20 wt % precipitate, more preferably at least about 23 wt % precipitate.

According to an embodiment in which a suspension of precipitate of the material to be processed is concentrated to form a cake, the yield of the material can be increased as follows. Following centrifugation, the liquid removed is stored and mixed with liquid from a subsequent centrifugation following re-suspension of the cake. Mixture of the two liquids may yield further precipitate, which can then be centrifuged and added to the existing cake. This can remedy selective precipitation of one of a plurality of species during cake formation, when such selective precipitation is unwanted.

Example 2 below describes preparation of finely divided aluminum-zirconium chlorohydrate material by precipitation from a solvent system including water and propylene glycol with a precipitating species including ethanol and acetone, displacement of solvent system/precipitating species with liquid $CO_2$ as an isolating species, and isolation of the material under supercritical conditions. Material having a surface area of 146.3 $m^2/g$ was collected. As comparative examples to demonstrate the importance of proper selection of the solvent system/precipitating species mixture, when pure acetone was used as a precipitating species, material having a surface area of approximately 50 m$^2$/g was collected (it should be noted that in many circumstances 50 m$^2$/g is more than adequate surface area). When pure ethanol was used as a precipitating species, material having a surface area of approximately 250 m$^2$/g was collected, but the material was depleted in aluminum chlorohydrate (it should be noted that in many circumstances it would be desirable to selectively deplete one material in a solution containing more than one).

According to one aspect of the invention, the solvent system/precipitating species is displaced from the material precipitate by the pure precipitating species prior to displacement by the isolating species and supercritical isolation. This is advantageous when the isolating species is not miscible with the solvent system. According to another aspect, the solvent system/precipitating species is displaced by another inert species that is miscible with the isolating species, and this is advantageous when neither the solvent system nor the precipitating species is miscible with the isolating species.

Described above are embodiments of the invention in which material is precipitated from a solvent system by a precipitating species and then supercritically isolated, or precipitated by a precipitating species which then is displaced by an isolating species, followed by supercritical isolation. According to one aspect of the invention, precipitation of the material can be effected by altering the temperature of a species within which the material is dissolved, followed optionally by displacement of that species with another inert species and then displacement by and supercritical isolation with the isolating species.

The inventive process results in aerogels having particularly desirable properties, for example particularly fine, high surface area product if no fluid phase/fluid phase interface is allowed to form at any stage of the process. As used herein, the term "fluid phase/fluid phase interface" is meant to define a phase boundary between two or more phases, more than one of which can contain the material to be processed. For example, such an interface may be defined between two or more of dense fluids or gasses during the mixing and precipitation step, or during the step of taking the precipitating species or isolating species above its supercritical point and exhausting. Thus, if the precipitating species or isolating species is introduced into the solution in a gaseous state in which the material to be processed does not reside, for example by bubbling the gas through the solution, this does not detract from the advantages of the invention. As used herein, "dense fluid" is meant to define a liquified gas, a pressurized vapor, or a supercritical fluid.

As noted above, a wide variety of materials may be selected for processing as aerogels according to the present invention. It is only necessary that the material be soluble, at least to some extent, in a solvent system selected in accordance with the present invention. For example, organic or inorganic materials, polymers, ceramics, ceramic precursors, pharmaceuticals, biological species, pigments, dyes, amorphous species, crystalline species, metal salts including hydroxides, chlorides and oxides, acetates, chlorohydrates, green bodies, dopants, and the like may be processed according to the invention. A non-limiting list includes zinc oxide, lithium iodide, fluorescein, erythromycin, benzofurfurin, cobalt phthalocyanate, aluminum chlorohydrate, aluminum-zirconium chlorohydrate, caprolactam thiazolidine, aluminum nitrate nonahydrate, copper chloride, eosin Y, fullerite, salicylic acid, and zinc acetate dihydrate.

Solvent systems suitable for use with the present invention may include a pure solvent, or may include a mixture of solvents if such solvents are miscible. Virtually any solvent system may be selected, as long as selection is made in accordance with criteria of the present invention regarding miscibility with the precipitating species and solubility of the material to be processed in the solvent system. Thus, polar, non-polar, protic, or aprotic solvents may be selected, for example, hydrocarbons, fluoro or perfluorohydrocarbons, alcohols, ketones, ethers, aldehydes, amines, amides, esters, water, or the like. If complete recovery of all components of the solvent system is desired, the solvent system should be selected so as to have a boiling point lower than the temperature at which displacement and recovery of solvent, described below, is effected.

A wide variety of isolating species may be used in the process of the present invention. It is important that the isolating species be miscible with the solvent system, if the isolating species and the precipitating species are the same, and with the precipitating species if the precipitating species and isolating species differ. Additionally, it is important that the material to be processed be at least partially insoluble in the isolating species, even above the isolating species' critical point, that the isolating species be inert with respect to the material to be processed, and that the critical temperature of the isolating species be a temperature at which significant degradation of the material to be processed does not occur. A book entitled *Supercritical Fluid Technology Reviews in Modern Theory and Applications*, by James C. Rainwater, Thomas J. Bruno and James F. Ely, Eds., C.R.C. Press, 1991, pp 78–79, incorporated herein by reference, lists a variety of compounds suitable for use as an isolating species of the present invention. For example, acetic acid, acetone and other ketones, ammonia, benzene, butane, carbon dioxide, carbon tetrachloride, ethane, ethyl alcohol, ethylene, ethyl ether, methyl ether, heptane, isobutane, isopropyl alcohol, methyl alcohol, nitrous oxide, octane, pentane, propane, propylene, and a variety of halogenated compounds such as refrigerants may be selected.

According to one embodiment of the invention, the precipitating species and isolating species are the same, and comprise a dense fluid that causes precipitation of the material to be processed. According to this embodiment, the dense fluid and solvent system are selected so as to be completely miscible, the dense fluid being selected to precipitate the material. The dense fluids then completely displaces the precipitating species, then is taken above its critical point, and exhausted above its critical temperature.

According to a preferred embodiment, the dense fluid is a liquified gas, and according to an especially embodiment, the gas selected is carbon dioxide. An article entitled "Ternary Systems of Liquid Carbon Dioxide", by Alfred W. Francis, Journal of Physical Chemistry, 58, 1099–1107 (1954), incorporated herein by reference, lists a variety of solvents suitable for use in the present invention when carbon dioxide is selected as the precipitating species or isolating species. In particular, the following solvents and/or mixtures thereof are preferred for use as solvents in the present invention when carbon dioxide is used as a precipitating species and isolating species: acetic acid, acetonitrile, acrylonitrile, amyl alcohol, aniline, benzene, sec-butyl alcohol, 2-butanone, caproic acid, caprylic acid, chlorobenzene, chloroform, a-chloronaphthalene, o-chlorophenol, p-chlorophenol, p-dichlorobenzene, 2,4-dichlorophenol, ethyl acetate, ethyl alcohol, 2-ethylhexanol, methyl ethyl ketone, naphthalene, nitrobenzene, o-nitrophenol, phenol, toluene, isopropanol, methanol, acetone, furfural, succinonitrile, and phenol.

Various particles made in accordance with the invention are shown in FIGS. 1–5.

Figure 7:
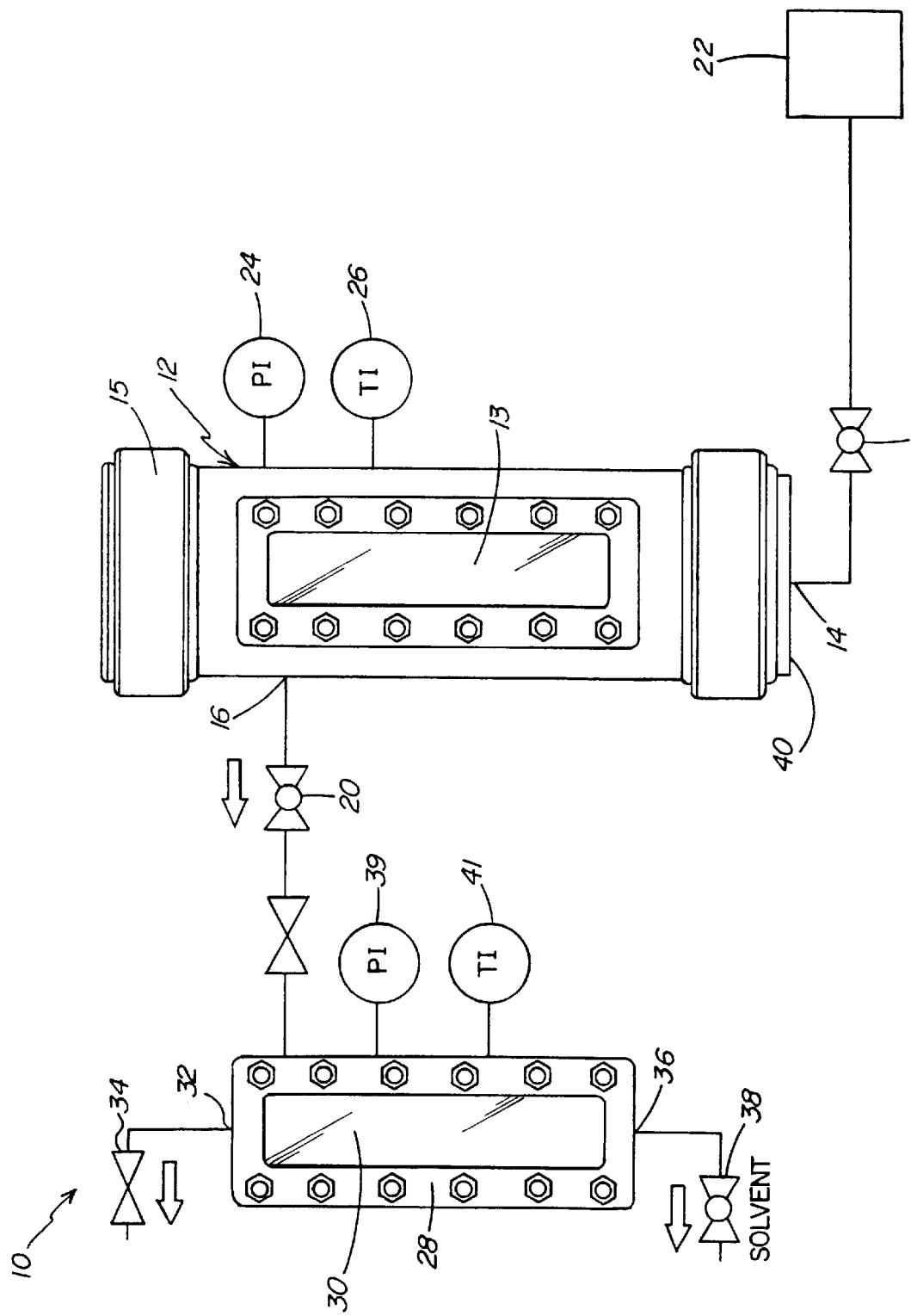
FIG. 7 is a schematic illustration of apparatus designed to prepare aerogel material according to one embodiment of the present invention.

Reference will now be made to FIG. 7, and an apparatus arrangement 10 for effecting the inventive method will be described. Referring to FIG. 7, apparatus 10 includes pressure vessel 12. Vessel 12 should be constructed to be large enough to process a predetermined amount of material, and should be constructed so as to be strong enough to withstand temperatures and pressures well above those involved in the precipitation and supercritical exhaustion steps of the invention. Vessel 12 may have a window 13 so that observation of the precipitation and washing steps may be viewed. This may be advantageous when solvent system is washed from the precipitate by introducing precipitating species and decanting the precipitating species/solvent system mixture, or introducing isolating species and decanting precipitating species as a precipitating species/solvent system mixture. The precipitates may be observed, and a flow rate selected that does not sweep away the product.

Vessel 12 includes inlet 14 and outlet 16, which may be located anywhere on the vessel 12. Outlet 16 may be equipped with a filter, not shown, such as a glass frit, or a sight gauge, analyzer, or the like. In this way, the flow of precipitating or isolating species through vessel 12 during the washing step may be effected without loss of material product. However, such a filter may become plugged, and it is often advantageous to provide outlet 16 high enough on vessel 12 so that decanting, as described above, may be effected. Inlet 14 is equipped with valve 18, and outlet 16 is equipped with valve 20. Thus, vessel 12 may be isolated. Inlet 14 communicates with source 22 of precipitating and/or isolating species, and source 22 may be equipped with a pump or the like (not shown). Vessel 12 is equipped with pressure indicator 24, and temperature indicator 26. Outlet 16, via valve 20, communicates with separating vessel 28, which may also be equipped with a window 30. Separating vessel 28 may have a gas outlet 32, regulated by valve 34, and a solvent recovery outlet 36, regulated by valve 38. Separating vessel 28 may also have a pressure indicator 39 and a temperature indicator 41, and may be equipped with temperature controlling means (not shown).

In the following description, an embodiment in which a gas serves as a precipitating and isolating species, introduced from source 22, is described. However, source 22 may schematically represent a source of separate precipitating and isolating species, either or both of which could be introduced as a gas, liquid, or supercritical fluid. During operation of apparatus 10 a pure solution, a solution containing a plurality of species, or a solution containing some precipitated species is introduced into vessel 12, either by removing top 15 thereof or by introducing the solution through a input connected to input 14 or another input. Then, with valve 20 closed, valve 18 is opened so as to introduce gas from source 22 into the vessel 12. If vessel 12 is maintained at a high enough pressure, a dense fluid, such as a liquefied gas, from source 22 may be introduced.

Precipitation can be effected by introducing a precipitating species through inlet 14, or another inlet (not shown) to precipitate material from solution in vessel 12. Alternately, precipitation may be effected and a slurry introduced into vessel 12. Once the material to be processed is fully precipitated in vessel 12, and vessel 12 is at a pressure high enough that the gas from source 22 is maintained therein in liquid form, valve 20 may be opened while additional precipitating species may be introduced into inlet 14. Thus, pure precipitating species is introduced into liquid 14, flows upward through the precipitated product in vessel 12, and a solvent system/precipitating species mixture exits at output 16. This continues until a predetermined amount of solvent system is removed from the material. According to preferred embodiments, virtually all of the solvent system is removed. Then, valve 20 is closed, the pressure in vessel 12 is adjusted through input 14 so as to be higher than the critical pressure of the precipitating species, valve 18 is closed, and heater 40 is activated to drive the temperature in vessel 12 above the critical temperature of the precipitating species. Once a supercritical fluid has been created in vessel 12, heater 40 acts to maintain the temperature in the vessel above the critical temperature of a precipitating species, and the supercritical fluid is exhausted by opening valve 20. Aerogel then is recovered from vessel 12.

Recovery of the solvent system, and determination of the degree of purity of product within the vessel 12, is carried out as follows. During the step of displacement of solvent system from vessel 12 by precipitating species, the solvent system/precipitating species mixture passes through valve 20 and into separation vessel 28. Separation vessel 28 is maintained under conditions of temperature and pressure such that the precipitating species is in a gaseous state, and the solvent system is in a liquid state, according to a preferred embodiment. Therefore, the precipitating species exits through top output 32, through valve 34, and may be recovered. The solvent system exits through bottom outlet 36, through valve 38, and may be recovered. If one material has been prepared in solution in vessel 12 to be processed, that is, a solution including but one species is introduced into vessel 12, and precipitating species is selected so as to fully precipitate material product, solvent system may be recovered through valve 38 in virtually pure form. In this case, the amount of solvent system recovered through valve 38 is indicative of the purity of product in vessel 12.

Described thus far is a batch process for preparing high-surface-area particulate material. However, a continuous process may also be practiced in accordance with the present invention. The continuous process may involve separate precipitating species and isolating species or, the precipitating species and isolating species may be the same. According to an embodiment in which the precipitating species and isolating species are the same, and in particular comprised of carbon dioxide, a solution or slurry is continuously fed into a pressure vessel and is mixed with carbon dioxide therein. Material to be processed is precipitated from the solution or slurry by the carbon dioxide, separated by decanting, centrifugal separation, filtering, or the like, washed with carbon dioxide, taken to supercritical conditions, and discharged through a pressure-let-down device above the critical temperature of carbon dioxide. Additionally, such a continuous process could be effected if separate precipitating species and isolating species were employed.

Figure 8:
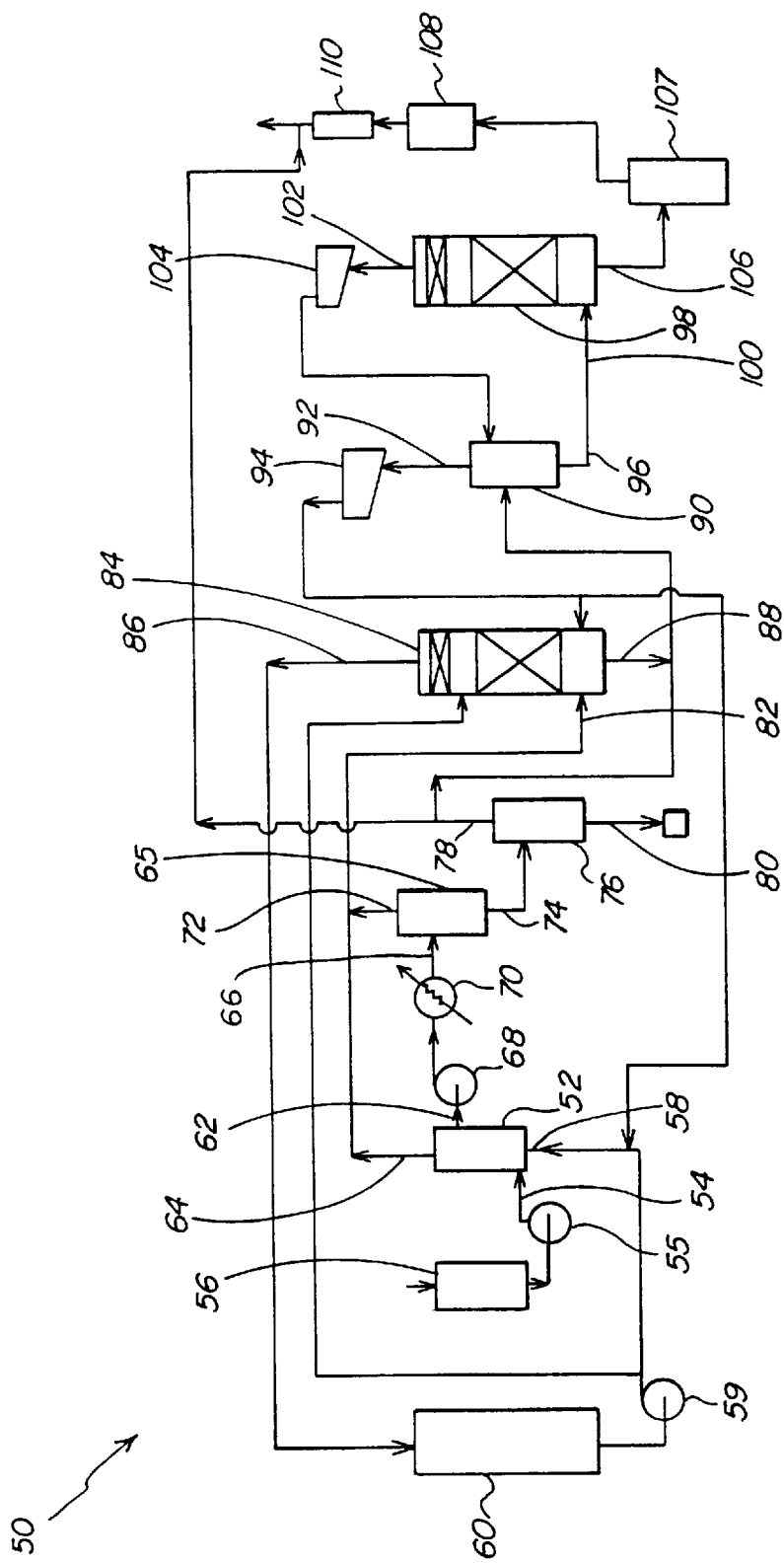
FIG. 8 is a schematic illustration of apparatus designed for continuous preparation of aerogel material according to one embodiment of the present invention.

Referring now to FIG. 8, apparatus 50 for continuous processing of aerogels in accordance with one embodiment of the invention is illustrated. Apparatus 50 is designed to provide continuous processing of aerogels according to an embodiment in which material is precipitated from solution with a precipitating species, the solvent system is displaced by the precipitating species, and the precipitating species then is taken above its critical point and exhausted above its critical temperature.

Apparatus 50 includes a precipitation vessel 52 having a solution inlet 54 that is connected via a feed booster pump 55 to a source 56 of solvent system having dissolved therein the material to be processed, and a precipitating species ($CO_2$) inlet 58 connected via a high pressure $CO_2$ pump 59 to a source 60 of $CO_2$. Precipitation vessel 52 has a precipitate outlet 62 located on the side of the vessel, and a solvent system/precipitating species outlet 64 located at the top of the vessel. Precipitate outlet 62 delivers to a pressure vessel 65 the precipitate carried by $CO_2$ through a pressure vessel inlet 66. A booster pump 68 and a high pressure heater 70, illustrated schematically between precipitate outlet 62 and pressure vessel inlet 66, serve to take the $CO_2$ containing the precipitate in pressure vessel 65 above its critical point to form a supercritical fluid. $CO_2$ then is exhausted above its critical temperature through exhaust outlet 72, at or near the top of pressure vessel 65, and aerogel is recovered through product recovery port 74 from the pressure vessel and into low pressure separator 76. A let-down valve (not shown) is arranged at or beyond port 74, vessels 65 and 76. Low pressure separator 76 provides for mild heating of the product to further drive off any residual solvent and to vent residual $CO_2$ through an outlet 78 located at or near the top of the separator, and delivers aerogel through an aerogel outlet 80 located at or near the bottom of the separator.

Solvent system/precipitating species outlet 64 and exhaust outlet 72 are connected to an inlet 82 of a $CO_2$ recovery vessel 84. Vessel 84 delivers $CO_2$ through an outlet 86 to source 60 of $CO_2$, and delivers solvent system containing residual $CO_2$ through an outlet 88 to a separator 90. Separator 90 separates $CO_2$ from the solvent system and delivers $CO_2$ to precipitating species inlet 58 of precipitation vessel 52, or to $CO_2$ recovery vessel 84, via an outlet 92 and a compressor 94. Residual solvent system is delivered from separator 90 via an outlet 96 to a second $CO_2$ recovery vessel 98 via an inlet 100. Recovery vessel 98 delivers $CO_2$ through an outlet 102 to separator 90 via a compressor 104, and residual solvent system is delivered from recovery vessel 98 via an outlet 106 to a solvent system recovery chamber 107. Vent separator 108 and vent purifier 110, connected to an outlet of solvent system recovery chamber 107, facilitate removal and venting of residual $CO_2$ from the solvent system.

In practice, a plurality of precipitation vessels 52 can be arranged in series, and a plurality of pressure vessels 65 arranged in series with a series of successive pressure let-downs, to maximize efficiency and aerogel recovery in the process. A series of successive vessels 76 can be employed as well. A solvent system/precipitating species outlet 64 of each precipitation vessel 52 feeds into an inlet of the next precipitation vessel in the series. An exhaust outlet 72 of each pressure vessel 65 feeds into an inlet of the next pressure vessel in the series. In this way, each of the precipitation vessels 52 in series produces precipitate in successively purer $CO_2$ (with solvent system removed), and each of the pressure vessels 65 in series produces successively dryer product. Alternatively, a precipitation vessel 52 can be arranged so as to precipitate material and efficiently separate the precipitate in nearly pure $CO_2$ from a solvent system/$CO_2$ mixture. For example, a relatively tall vessel 52 having a $CO_2$ input at or near the bottom and a solution input at or near the top of the vessel will facilitate upward flow of $CO_2$, downward flow of solution, precipitation between the solution inlet and the $CO_2$ inlet, removal of precipitate in $CO_2$ from an outlet near the bottom of the vessel, and recovery of solvent system/$CO_2$ mixture from an outlet near the top of the vessel. Flow rates can be adjusted so as to allow product to be removed from the product outlet, a membrane or filter can be used, or the like. Similarly, a large pressure vessel 65 can be constructed that produces dry product.

Not shown in FIG. 8 are those components, such as valves, that one of ordinary skill in the art would recognize, in part from the description above with respect to FIG. 8, as necessary for implementing the apparatus.

EXAMPLES

The function of the embodiments described herein and other embodiments of the invention will be more fully understood from the examples. The examples are intended to illustrate the benefits of the present invention, but do not exemplify the full scope of the invention. Additional embodiments and advantages within the scope of the claimed invention will be apparent to those of ordinary skill in the art.

Example 1

Aluminum Chlorohydrate in Aerogel Form

Aluminum chlorohydrate (ACH) aerogel was prepared by precipitating ACH from a solvent system with a precipitating species, and isolating the material under supercritical conditions.

A standard 50% aqueous solution of 5/6 basic ACH was freeze dried according to conventional methods. The freeze dried ACH material was reduced to a fine powder using a mortar and a pestle.

A solvent system of isopropanol/water and denatured ethanol was prepared as follows: 59 ml of 70 vol % isopropanol/30 vol % water was added to 1341 g (1700 ml) of ethanol (200 proof SDA 3, which is made by adding 5 gallons of methanol to 100 gallons of ethanol; chromatographic analysis indicated that traces of other unidentified compounds were also present). Therefore, the ratio of water to alcohol was about 1:100 by volume.

240 grams of the ground ACH material were added to the solvent system which then was stirred for 24 hrs, after which time most of the ACH material had dissolved. The color of the resulting system was white opaque. A thick sludge settled on the bottom of the container after stirring was stopped and the system was allowed to stand for at least 4 hrs. The sludge then was separated and the resulting solution was transparent and slightly opalescent, foaming slightly upon shaking. The concentration of ACH in the solution was 8.6 wt %. The solution density was 0.87 g/ml. The total weight of sludge collected was 49.8 g, 44 wt % of which was ACH.

1.71 of the solution was introduced into a one gallon stainless steel windowed pressure vessel equipped with an inlet line located in the middle of the bottom of the vessel, an outlet line located on the side of the vessel ¼ of the distance from its top, a pressure gauge, a thermocouple, and a pressure relief valve (1500 psi).

$CO_2$ was selected as a precipitating species and was introduced as a vapor into the system through the inlet line from a 50 lb. cylinder equipped with an eductor tube. The pressure in the cylinder at room temperature was approximately 800 psi, and as the pressure in the vessel was increased to the pressure of the cylinder the solution was kept homogeneous using a magnetic stirrer. At 800 psi, the liquid level in the vessel had increased to 2.8 liters due to $CO_2$ dissolution in the alcohol/water/ACH solution. As the $CO_2$ concentration in the solution increased, ACH precipitated. At 800 to 850 psi, the ACH precipitate began to agglomerate, at which time stirring was stopped. The contents of the vessel appeared solid with a total volume of about 3 liters.

Liquid $CO_2$ then was pumped into the vessel through the inlet line using an air driven, double acting Haskel pump, to isolate the material. The pressure was increased to about 950 psi while the temperature was maintained at room temperature. The alcohol/water system was displaced from the material in the vessel by pumping fresh $CO_2$ into the vessel through the inlet line and removing a mixture of $CO_2$, alcohol, and water from the outlet line. The outline was connected to a separator maintained at a pressure of 100 psi and a temperature of between about −2° C. and −15° C. Under these conditions $CO_2$ was vented as a vapor and the alcohol/water solution was collected as a liquid. The average mass flow rate of $CO_2$ during this solvent replacement period was about 35 to 40 g/min. The flow was manually adjusted so that particulates were not carried out with the liquid stream through the outlet line.

The degree of replacement of solvent in the vessel by liquid $CO_2$ was determined by measuring the amount of the solvent system collected via the separator. When the concentration of alcohol/water in the ACH material was about 10–15% by volume, heat was added to the system using a heating ring attached to the bottom cover. Power was set at 20 w. The pressure increased regularly as the temperature increased, and $CO_2$ flow was maintained constant. Solvent system displacement was continued until about 95% of the original solvent system was collected as a liquid. At this point the concentration of ethanol in the ACH material was less than 2%, the temperature in the vessel was close to 104° F. (40° C.) and the pressure was 1200 psi.

The heat input was increased to 450 w. The $CO_2$ inlet stream was closed. The temperature was maintained above 104° F. and the pressure was reduced slowly to atmospheric pressure. The vessel then was opened and dry ACH powder was collected.

The ACH collected had a surface area of 106 $m^2/g$; a bulk density of 0.36 g/cc (ASTM C493-86); an absolute density of 0.57 g/cc; a percent pore of about 37%; a pore volume of 0.43 cc/g; an average pore size of 322 nm; and a particle size of 0.04 micron–0.08 micron.

Example 2

Aluminum-Zirconium Chlorohydrate in Aerogel Form

Finely divided aluminum-zirconium chlorohydrate material was prepared by precipitating the material from a solvent system with a precipitating species, displacement of solvent system/precipitating species with an isolating species, and isolation of the material under supercritical conditions.

An aluminum/zirconium stock solution was prepared by diluting with water to 10% a standard 50% ACH solution and heating at about 85° C. for 16–17 hours. A sufficient volume of an aqueous solution of ZrO[OH]Cl (complexed with glycine, 1:1) was added to the 10% ACH solution to provide a solution with an Al:Zr ratio of about 3.6. The ZrO[OH]Cl solution can be purchased from standard sources or prepared by conventional methods. A sufficient volume of propylene glycol then was added to provide a solution containing about 73% water, about 12% Al/Zr salt, and about 15% propylene glycol. Water then was evaporated to provide a stock solution of Al/Zr material in a solvent system of water and propylene glycol. The stock solution included about 41% Al/Zr salt, about 11% water, and about 48% propylene glycol.

Ethanol/acetone was selected as a precipitating species. 332 g of stock solution were mixed with 675 g of SDA 3 ethanol and 1122 g acetone, whereupon most of the salt precipitated and was centrifuged. After centrifugation, 342 g of centrifugate (a cake containing about 20 wt % salt and the remainder solvent system/precipitating species) were mixed with 1050 g of acetone, and the suspension was centrifuged a second time.

208 g of centrifugate were mixed with 540 g of ethanol. The resulting suspension then was introduced to a pressure vessel (apparatus similar to that described in Example 1, with the exception that the vessel had no window). $CO_2$, selected as an isolating species, was added to the vessel through the inlet line, and the pressure was rapidly raised to 950 psi. Solvent system/precipitating species was displaced from the vessel by liquid $CO_2$ and separated, in a manner similar to that in Example 1, with the exception that the average mass flow rate in the vessel was reduced to prevent precipitate from being swept away with the outlet stream. The $CO_2$ was taken above its critical point and exhausted above its critical temperature as described in Example 1. The resulting aerogel had a surface area of 146.3 $m^2/g$; a bulk density of 0.29 g/cc (ASTM C493-86); an absolute density of 2.1 g/cc; a pore volume of 0.73 cc/g; a percent pore of 86%; an average pore size of 20 nm; and a particle size range of 0.005 micron–0.1 micron.

Example 3

Al/Zr Salt in Aerogel Form 171 g of stock Al/Zr solution as prepared in example 2 were mixed with a precipitating species including 360 g of ethanol and 1470 g of acetone, and the salt precipitated. After centrifugation, 340 g of centrifugate were washed with 570 g acetone and centrifuged a second time. Two more batches were prepared in this way, and the centrifugates were combined. 848 g centrifugate were mixed with 1100 g ethanol and processed as previously described. The yield was 160 grams.

The Al/Zr aerogel salt had a surface area of 61 $m^2/g$; a bulk density of 0.52 g/cc (ASTM C493-86); an absolute density of 2.0 g/cc; a pore volume of 0.5 cc/g; a percent pore of 74%; an average pore size of 26 nm; and particle size range of 0.06 micron–0.12 micron.

Example 4

Caprolactam thiazolidine in Aerogel Form

Caprolactam thiazolidine was precipitated in 800 ml of toluene, and stood for 48 hours. The system was free of water. The toluene above the precipitate was removed and 310 g of caprolactam thiazolidine sludge was introduced into a vessel 12 similar to that described in Example 1, with the exception that the outlet line was equipped with a fritted glass filter. $CO_2$ as an isolating species was introduced into the bottom of the vessel 12, toluene was displaced and the precipitate was washed with $CO_2$ as described above in Example 1. When the caprolactam thiazolidine was essentially free of toluene, the inlet stream was closed. $CO_2$ was taken above its critical point, then the pressure was reduced slowly to atmospheric pressure. Eighteen grams of light yellow powder were collected.

Example 5

Aluminum Nitrate Nonahydrate in Aerogel Form

Aluminum nitrate nonahydrate ($Al(NO_3)_3.9H_2O$) has a high solubility in EtOH but low in acetone. 1.9 g $Al(NO_3)_3.9H_2O$ was almost completely dissolved in a solvent system including a mixture of 36 g EtOH and 70 g acetone. According to the procedure described in Example 1, the material was precipitated from the clear solution by $CO_2$, the solvent system was displaced, and dry, white hygroscopic powder was isolated under supercritical conditions.

Example 6

Copper (II) Chloride in Aerogel Form 7 g copper chloride ($CuCl_2$; anhydrous) was dissolved in 10 g EtOH, yielding a characteristically green solution. According to the procedure described in Example 1, the material was precipitated from solution by $CO_2$, the solvent system was displaced, and brown powder was isolated under supercritical conditions.

Example 7
Eosin Y in Aerogel Form 0.7 g Eosin Y (Acid Red 87, D&C Red No. 22) was dissolved in 17.5 g EtOH, forming a deep red solution. According to the procedure described in Example 1, the material was precipitated from solution by $CO_2$, the solvent system was displaced, and bright red powder was isolated under supercritical conditions. The powder had a bulk density of 0.08 g/cc (measured as mass/volume under ambient conditions).

Example 8
Fullerite in Aerogel Form 15 g toluene was used to dissolve 0.11 g fullerite ($C_{60}$ and $C_{70}$; $C_{60}/C_{70}=9/1$), producing a saturated dark brown solution. According to the procedure described in Example 1, the material was precipitated from solution by $CO_2$, the solvent system was displaced, and dark brown powder was isolated under supercritical conditions. The powder had a bulk density of 0.1 g/cc (measured as mass/volume under ambient conditions).

Example 9
Salicylic Acid in Aerogel Form

A total of 8 ml acetic acid was added to completely dissolve 5 g salicylic acid (sodium salt) in 50 g EtOH. According to the procedure described in Example 1, the material was precipitated from solution by $CO_2$, the solvent system was displaced, and white to light yellow powder was isolated under supercritical conditions.

Example 10
Zinc Acetate Dihydrate in Aerogel Form 2.5 g zinc acetate dihydrate ($ZnAc_2.2H_2O$) was dissolved in 60 g boiling EtOH, some of which re-precipitated when cooled to room temperature. According to the procedure described in Example 1, the material was precipitated from a saturated solution by $CO_2$, the solvent system was displaced, and white powder was isolated under supercritical conditions. The powder had a bulk density of 0.06 g/cc (measured as mass/volume under ambient conditions), and a surface area of 20 $m^2/g$.

Antiperspirant Compounds

As noted above, according to one embodiment the invention relates to antiperspirant compounds that are in aerogel form. The preferred aerogel antiperspirant compounds have a surface area of about 50 $m^2/g$ to about 1200 $m^2/g$, a bulk density of about 0.01 g/cc to about 1.75 g/cc (ASTM C493-86), a pore volume of about 0.15 cc/g to about 1.9 cc/g, and an average particle size of about 0.005 micron to about 0.07 micron. More preferred aerogel antiperspirant compounds have a surface area of about 100 $m^2/g$ to about 1000 $m^2/g$, a bulk density of about 0.1 g/cc to about 0.5 g/cc (ASTM C493-86), an average particle size of about 0.005 to about 0.07 micron, and a pore volume of about 0.15 cc/g to about 1.7 cc/g.

Preferred antiperspirant compounds are metal salts that have significant antiperspirant activity when applied to the skin of a human, and include various inorganic and organic salts of aluminum, zirconium, and zinc. Many examples of these salts are known to those skilled in the art.

The preferred salts are any of the conventional aluminum, zirconium and aluminum-zirconium salts known to be useful in antiperspirant compositions. These salts include aluminum halides and aluminum hydroxy halides (e.g., aluminum chlorohydrate), and mixtures or complexes thereof with zirconyl oxyhalides and zirconyl hydroxyhalides (e.g. aluminum-zirconium chlorohydrate).

Preferred aluminum salts are those having the general formula $Al_2(OH)_{6-a}X_a \cdot nH_2O$ wherein X is Cl, Br, I or $NO_3$, a is about 0.3 to about 4, preferably about 1 to 2, such that the Al to X mole ratio is about 1/1 to 2.1/1, and n is 1 to 6, preferably about 2. Most preferably, the aluminum salt is aluminum chlorohydrate (i.e., X is Cl) and a is about 1, such that the aluminum to chlorine mole ratio is about 1.9/1 to 2.1/1.

Preferred zirconium salts have the formula $ZrO(OH)_{2-pb}Y_b \cdot mH_2O$ wherein Y is Cl, Br, I, $NO_3$, or $SO_4$, b is about 0.8 to 2, p is the valence of Y, and m is about 1 to 7. Preferably the zirconium salt is zirconyl hydroxychloride of the formula $ZrO(OH)_{2-b}Cl_b \cdot mH_2O$ wherein b is about 1 to 2, preferably about 1.2 to about 1.9.

Preferred antiperspirant compounds also include mixtures and complexes of the above aluminum and zirconium salts. If such complexes are used, it is preferred that it have an Al:Zr ratio of about 1.67 to about 12.5, most preferably about 2 to 6, and a metal:X ratio of about 0.73 to about 2.1, preferably about 0.9 to 1.5. A preferred salt is aluminum zirconium chlorohydrate (i.e., X and Y are Cl), which has an Al:Zr ratio of about 2 to 6 and a metal:Cl ratio of about 0.9 to 2.1. Such complexes may also contain a neutral amino acid, preferably glycine.

It is especially preferred to use high efficacy forms of aluminum and aluminum-zirconium salts such as those described, for example, in GB 2,048,229, EP 405,598, U.S. Pat. No. 4,359,456, U.S. Pat. No. 4,775,528, U.S. Pat. No. 4,871,525, U.S. Pat. No. 4,859,446, U.S. Pat. No. 4,900,534, U.S. Pat. No. 4,944,933, U.S. Pat. No. 5,202,115, U.S. Pat. No. , 5,234,677, U.S. Pat. No. 5,296,623, and U.S. Pat. No. 5,330,751. Such salts, when reconstituted as 10% aqueous solutions, typically produce an HPLC chromatogram wherein at least 80% of the aluminum is contained in two successive peaks, conveniently labeled peaks 3 and 4, wherein the ratio of the area under peak 4 to the area under peak 3 is at least 0.70, preferably at least 1.0 or higher. A preferred aluminum-zirconium chlorohydrate (Al/Zr) solution that can be used in providing a Al/Zr aerogel salt comprises (by weight) between about 40–45% Al/Zr salt, about 44–50% propylene glycol, and about 10–13% water.

Antiperspirant compounds can be converted to aerogel form according to the general procedures for preparing aerogels described previously. Examples 1–3 are representative.

Antiperspirant and Deodorant Compositions

The aerogel antiperspirant compounds may be incorporated into any conventional antiperspirant or deodorant composition, including solid sticks, semi-solid sticks, gel sticks, aerosols, roll-ons, and creams. Generally, such compositions will comprise an antiperspirant or deodorant effective amount of the aerogel antiperspirant compound. Antiperspirant compositions typically include between about 4% and 30% (preferably between about 8% and 22%) of the aerogel antiperspirant compound, with the remainder substantially comprising the carrier. Deodorant compositions typically include between about 1% and 6% of the aerogel antiperspirant compound. Other components which may be utilized in the antiperspirant or deodorant compositions may be any of those which are conventionally known for use in formulating antiperspirant and deodorant compositions. These ingredients, for example, include emollients, thickeners, fragrances, dyes, preservatives, solidifying or gelling agents, fillers, emulsifiers, humectants, and talc.

The carrier commonly used in solid stick antiperspirant compositions includes a high melting component and a low melting component. Typical of high melting components are the high melting point waxes. These include beeswax, spermaceti, carnauba, bayberry, candelilla, montan, ozokerite, ceresin, and paraffin waxes, synthetic waxes such as Fisher-Tropsch waxes, semimicrocrystalline and microcrystalline waxes, hydrogenated jojoba oil, and hydrogenated castor oil (castor wax). The preferred wax is hydrogenated castor oil. Other suitable high melting components include various types of high melting gelling agents such as polyethylene-vinylacetate copolymers and polyethylene homopolymers. Typically, the high melting components comprise about 1 to 25%, preferably about 2 to 15%, of the antiperspirant stick.

Typical of low melting components commonly used in solid stick antiperspirant compositions are volatile silicones, non-volatile silicones, $C_{3-6}$ diols, fatty alcohols, fatty alcohol esters, fatty acid esters, fatty amides, non-volatile paraffinic hydrocarbons, polyethylene glycols, polypropylene glycols, polyethylene and/or polypropylene glycol ethers of $C_{4-20}$ alcohols, polyethylene and/or polypropylene glycol esters of fatty acids, and mixtures thereof. The term "fatty" is intended to include hydrocarbon chains of about 8 to 30 carbon atoms, preferably about 12 to 18 carbon atoms. An especially preferred combination of low melting components comprises a volatile silicone, a low melting point wax, and a non-volatile emollient.

Volatile silicones include the cyclic polydimethylsiloxanes, also known as cyclomethicones, which have from about 3 to about 7 silicon atoms, and the linear polydimethylsiloxanes, also known as dimethicones, which have from about 2 to about 9 silicon atoms. The linear volatile silicones generally have viscosities of less than about 5 centistokes at 25° C., while the cyclic volatile silicones have viscosities under 10 centistokes. "Volatile" means that the material has a measurable vapor pressure at room temperature. Preferred are the cyclomethicones such as DC 344 and DC 345, available from Dow Corning Corporation.

Non-volatile silicones include polyalkylsiloxanes, polyalkylaryl siloxanes, and polyethersiloxane copolymers with viscosities of about 5 to about 100,000 centistokes at 25° C. These include polydimethylsiloxanes with viscosities of about 10 to about 400 centistokes at 25° C. (e.g. DC 200), polymethylphenylsiloxanes with viscosities of about 15 to about 65 centistokes, and polyoxyalkyleneether dimethyl siloxane copolymers with viscosities of about 1200 to about 1500 centistokes.

Useful $C_{3-6}$ diols include propylene glycol, butylene glycol, dipropylene glycol and hexylene glycol. Fatty alcohols include stearyl alcohol, cetyl alcohol, myristyl alcohol, oleyl alcohol, and lauryl alcohol. Fatty alcohol esters include $C_{12-15}$ alcohols benzoate, myristyl lactate, cetyl acetate, and myristyl octanoate. Fatty amides include stearamide, stearamide MEA, stearamide MEA-stearate, lauramide DEA, and myristamide MIPA.

Non-volatile paraffinic hydrocarbons include mineral oils and branched chain hydrocarbons with about 16 to 68, preferably about 20 to 40, carbon atoms. A preferred material is hydrogenated polyisobutene with about 24 carbon atoms. Suitable polyethylene glycols and polypropylene glycols will typically have molecular weights of about 500 to 6000, such as PEG-10, PEG-40, PEG-150 and PPG-20. Polyethylene and/or polypropylene glycol ethers of $C_{4-20}$ alcohols include PPG-10 Butanediol, PPG-14 Butyl Ether, PPG5-Buteth-7, PPG-3-Isosteareth-9, PPG-3-Myreth-3, Oleth-10, and Steareth-20. Polyethylene and/or polypropylene glycol esters of fatty acids include PEG-8 Distearate, PEG-10 Dioleate, and PPG-26 Oleate, and isopropyl esters such as isopropyl myristate and isopropyl palmitate.

A typical solid stick antiperspirant composition contains about 10 to 30% aerogel antiperspirant compound, about 25 to 45% cyclomethicone, about 13 to 18% stearyl alcohol, about 25 to 35% $C_{12-15}$ alcohols benzoate, and about 2 to 4% hydrogenated castor oil.

The carrier used in semi-solid or gel stick antiperspirant compositions generally includes no high melting component. Suitable carriers include the low-melting components (e.g., volatile silicones) described previously. A typical semi-solid or gel stick composition includes between 8% and 30% aerogel antiperspirant compound, between about 50% and 80% volatile silicone, and between about 10% and 50% $C_{12-15}$ alcohol benzoates.

Liquid antiperspirant compositions commonly are used in roll-on and in pump spray applicators. Any conventional anhydrous carrier commonly used in liquid antiperspirant compositions can be used. Preferred carriers include volatile silicone fluids and non-volatile silicone fluids such as those described previously. Significantly, liquid antiperspirant compositions of the invention optionally do not have to include a suspending agent because the antiperspirant compound is in the form of an aerogel and as a result is easily suspended in the carrier and stays suspended for a prolonged period. optionally, however, conventional suspending agents such as clays and colloidal pyrogenic silica (e.g., Cab-O-Sil) may be included in the composition. A typical liquid antiperspirant composition includes between about 6% and 30%, preferably about 8% and 22%, aerogel antiperspirant compound, with the remainder comprising substantially the anhydrous vehicle, which generally includes at least some volatile silicone.

The aerosol antiperspirant compositions can include the same types of anhydrous carriers used in liquid antiperspirant compositions. The aerosol compositions also include a propellant material. The propellant generally can be any liquefiable gas conventionally used for aerosol containers. Examples of such materials are trichlorofluoroethane, monochlorodifluoromethane, trichlorotrifluoroethane, dimethylether, propane, butane, and isobutane.

Examples 11–16 are meant to illustrate the invention particularly with respect to antiperspirant compounds in aerogel form. The aerogel ACH salt used in the examples is from example 1; the aerogel Al/Zr salt was from example 3.

Examples 11–13—Solid Sticks

|  | Weight % | | |
| --- | --- | --- | --- |
| Ingredient | Example #11 | Example #12 | Example #13 |
| Finsolv TN | 33.0 | 30.0 | 30.0 |
| Cyclomethicone | 30.0 | 43.0 | 43.0 |
| Aerogel (ACH) | 20.0 | 10.0 | — |
| Stearyl alcohol | 14.2 | 14.0 | 14.0 |
| Castor wax | 2.8 | 3.0 | 3.0 |
| Aerogel (Al/Zr) | — | — | 10.0 |

The Finsolv TN and the cyclomethicane were combined and mechanically stirred until homogenous. The homogeneous mixture was heated from room temperature to about 60° C. over 15 minutes. At that point the castor oil and stearyl alcohol were added and after the addition the mixture was heated to about 85° C. with agitation to provide complete homogeneity. The aerogel salt was added slowly to the mixture at 85° C. with vigorous mechanical and side-wall agitation. The salt was self-suspending. The mixture then was cooled to about 65° C. (at which point a fragrance optionally can be added), poured into suitable containers, and allowed to solidify.

The hardened solid stick compositions were applied to the skin. The composition displayed excellent application aesthetics and did not leave a white, flaky residue.

Example 14—Semi-Solid Stick

| Ingredient | Weight % |
|---|---|
| Cyclomethicone | 70.0 |
| Finsolv TN | 20.0 |
| Aerogel (ACH) | 10.0 |

The cyclomethicone and Finsolv TN were combined and mechanically stirred at room temperature until homogeneous. The aerogel antiperspirant compound was added slowly at room temperature with vigorous mechanical agitation and side-wall agitation to insure complete homogeneity. Importantly, the aerogel salt was self-suspending, which means that conventional suspending agents, emulsifiers, etc. were not used in formulating the composition. The mixtures were poured into suitable containers.

Example 15—Liquid

| Ingredient | Weight % |
|---|---|
| Cyclomethicone | 92.0 |
| Aerogel (ACH) | 8.0 |

The cyclomethicone and the aerogel antiperspirant compound were mixed at room temperature, with vigorous mechanical and side-wall agitation. Significantly, because the aerogel salt is self-suspending, conventional suspending agents and emulsions were not used in formulating the composition. The resulting mixture was poured into suitable containers (roll-on and pump spray) and can be applied to the skin in a conventional manner.

Example 16—Aerosol

| Ingredient | Weight % |
|---|---|
| Volatile silicone DC-344 | 36.0 |
| ACH aerogel | 4.0 |
| Hydrocarbon propellant A-31 | 60.0 |

The volatile silicone DC-344 and aerogel antiperspirant compound were mixed until uniform. The mixture was passed through a homogenizer/disperser one time. The aerogel salt was self-suspending and had a long settling time. The mixture was poured into a can and the pressurized gas added.

During application to the skin the composition displayed excellent spray attributes; the composition provided a dry, smooth feeling spray, and dried quickly after application.

The preceding examples are set forth to illustrate specific embodiments of the invention and are not intended to limit the scope of the invention. Additional embodiments and advantages within the scope of the claimed invention will be apparent to those of ordinary skill in the art.

What is claimed is:

1. A method of forming particulate material comprising:
    (a) selecting an anti-solvent within which the material is insoluble and inert;
    (b) selecting a solvent system within which the material is soluble and with which the anti-solvent is miscible;
    (c) forming a solution by providing the material in the solvent system;
    (d) contacting the solution with the anti-solvent to precipitate the material, the mixture of the anti-solvent and solvent system being maintained free of fluid-phase/fluid-phase interface;
    (e) displacing the mixture of the anti-solvent and solvent system with additional anti-solvent while avoiding any fluid-phase/fluid-phase interface during displacement to form a mixture of anti-solvent and material precipitate;
    (f) taking the anti-solvent and material precipitate mixture of step (e) above the critical point of the anti-solvent so as to form a supercritical fluid containing the material precipitate; and
    (g) exhausting the supercritical fluid at a temperature higher than the critical temperature.

2. The method as recited in claim 1, step (d) comprising: supplying the anti-solvent in step (d) in gaseous form.

3. The method as recited in claim 1, and further comprising, between steps (e) and (f), the step of:
    washing the material precipitate with additional anti-solvent until the material precipitate is substantially free of the solvent system.

4. The method as recited in claim 3, the washing step comprising:
    washing the material precipitate with the anti-solvent while retaining the material precipitate with use of a filter.

5. The method as recited in claim 3, the washing step comprising:
    washing the material precipitate with the anti-solvent by introducing the anti-solvent into a container within which the material resides, and decanting overflow therefrom.

6. The method as recited in claim 1, step (b) comprising selecting a solvent system in which the material has a solubility of at least 50 weight percent.

7. The method as recited in claim 1, step (a) comprising:
    selecting an anti-solvent, the material having a solubility in said anti-solvent of less than 1 weight percent.

8. The method as recited in claim 1, step (a) comprising:
    selecting an anti-solvent having a critical temperature lower than the degradation temperature of the material.

9. The method as recited in claim 1, step (a) comprising selecting an anti-solvent having at least 50 mol percent carbon dioxide.

10. A method of forming particulate material comprising:
    (a) selecting a supercritical anti-solvent within which the material is insoluble and inert;
    (b) selecting a solvent system within which the material is soluble and with which the supercritical anti-solvent is miscible;
    (c) forming a solution bv providing the material in the solvent system;
    (d) contacting the solution with the supercritical anti-solvent to precipitate the material;
    (e) displacing the mixture of the supercritical anti-solvent and solvent system with additional supercritical antisolvent to form a mixture of supercritical anti-solvent and material precipitate;

(f) maintaining the supercritical anti-solvent and material precipitate mixture of step (e) above the critical point of the anti-solvent; and (g) exhausting the supercritical anti-solvent at a temperature higher than the critical temperature.

11. The method as recited in claim 10, step (d) comprising:

contacting the solution with the supercritical anti-solvent the mixture of the supercritical anti-solvent and solvent system being maintained free of a fluid-phase/fluid-phase interface.

12. The method as recited in claim 10, step (e) comprising:

introducing the additional supercritical anti-solvent into a container containing the mixture of the supercritical anti-solvent and solvent system while decanting a mixture of the supercritical anti-solvent and solvent system.

13. A method of preparing particulate material comprising:

(a) selecting a supercritical isolating species within which the material is insoluble and inert;

(b) selecting a solvent system within which the material is soluble;

(c) selecting an anti-solvent that precipitates the material and within which the supercritical isolating species is miscible, (d) forming a solution by providing the material in the solvent system;

(e) contacting the solution with the anti-solvent to precipitate the material, the mixture of the anti-solvent and solvent system being maintained free of fluid-phase/fluid-phase interface;

(f) displacing the mixture of the anti-solvent and solvent system with the supercritical isolating species to form a mixture of supercritical isolating species and material precipitate;

(g) maintaining the supercritical isolating species and material precipitate mixture of step (f) above the critical point of the isolating species; and (h) exhausting the supercritical isolating species at a temperature higher than the critical temperature.

14. The method as recited in claim 13, wherein in step (e) the anti-solvent is supplied in gaseous form, and in step (f) the isolating species is supplied as a liquefied gas, said isolating species being gaseous at standard temperature and pressure.

15. The method as recited in claim 13, wherein the isolating species is carbon dioxide.

16. A method of preparing particulate material comprising:

(a) selecting an isolating species within which the material is insoluble and inert;

(b) selecting a solvent system within which the material is soluble;

(c) selecting an anti-solvent that precipitates the material and within which the isolating species is miscible;

(d) forming a solution by providing the material in the solvent system;

(e) contacting the solution with the anti-solvent to precipitate the material, the mixture of the anti-solvent and solvent system being maintained free of fluid-phase/fluid-phase interface;

(f) displacing the mixture of the anti-solvent and solvent system with the isolating species while avoiding any fluid-phase/fluid-phase interface during displacement to form a mixture of isolating species and material precipitate;

(g) taking the isolating species and material precipitate mixture of step (f) above the critical point of the isolating species so as to form a supercritical fluid containing the material precipitate; and (h) exhausting the supercritical fluid at a temperature higher than the critical temperature.

17. The method as recited in claim 16, further comprising, subsequent to step (e), the step of displacing the solvent system with the anti-solvent.

18. The method as recited in claim 16, further comprising, subsequent to step (e), the step of concentrating the resulting mixture of the anti-solvent/solvent system and the material precipitate to form a cake of precipitate.

* * * * *